United States Patent [19]
Stone et al.

[11] Patent Number: 5,306,311
[45] Date of Patent: * Apr. 26, 1994

[54] PROSTHETIC ARTICULAR CARTILAGE

[75] Inventors: Kevin R. Stone, Mill Valley, Calif.; Shu-Tung Li, Oakland, N.J.

[73] Assignee: ReGen Corporation, San Francisco, Calif.

[*] Notice: The portion of the term of this patent subsequent to Apr. 16, 2008 has been disclaimed.

[21] Appl. No.: 809,003

[22] Filed: Dec. 17, 1991

Related U.S. Application Data

[63] Continuation-in-part of Ser. No. 520,027, May 19, 1990, which is a continuation-in-part of Ser. No. 317,951, Mar. 2, 1989, Pat. No. 5,007,934, which is a continuation-in-part of Ser. No. 75,352, Jul. 20, 1987, Pat. No. 4,880,429.

[51] Int. Cl.⁵ .............................................. A61F 2/32
[52] U.S. Cl. .......................................... 623/18; 623/16
[58] Field of Search .................. 623/1, 13, 15, 17, 16, 623/18, 19, 20, 66

[56] References Cited

U.S. PATENT DOCUMENTS

| | | |
|---|---|---|
| 3,443,261 | 5/1969 | Battista et al. |
| 3,551,560 | 12/1970 | Thiele ................... 424/95 |
| 3,855,638 | 12/1974 | Pilliar ........................ 3/1 |
| 4,055,862 | 11/1977 | Farling ..................... 3/191 |
| 4,060,081 | 11/1977 | Yannas et al. ............ 128/156 |
| 4,064,567 | 12/1977 | Burstein et al. ............. 3/1.9 |
| 4,280,954 | 7/1981 | Yannas et al. ............ 260/123 |
| 4,291,013 | 9/1981 | Wahlig et al. ............. 424/16 |
| 4,350,629 | 9/1982 | Yannas et al. ........... 260/123.7 |
| 4,385,404 | 5/1983 | Sully et al. ................ 3/1.9 |
| 4,400,833 | 8/1983 | Kurland ...................... 3/1 |
| 4,418,691 | 12/1983 | Yannas et al. ............ 128/156 |
| 4,448,718 | 5/1984 | Yannas et al. ............ 260/123 |
| 4,458,678 | 7/1984 | Yannas et al. ............ 128/155 |

(List continued on next page.)

FOREIGN PATENT DOCUMENTS

| | | |
|---|---|---|
| 1170001 | 7/1984 | Canada . |
| 0277678 | 8/1988 | European Pat. Off. . |
| 8910738 | of 0000 | PCT Int'l Appl. . |
| 1515963 | 6/1978 | United Kingdom . |
| 8303536 | 10/1983 | World Int. Prop. O. . |

OTHER PUBLICATIONS

Petite and Rault J. Biomed. Mat. Res. (1990) 24:179–187.
Rubash et al. Clin. Orth. Rel. Res. 271:2–96.
Sengupta et al. J. Bone Surg. (1974) 56B 1:167–177.
Rodrigo et al. Cli. Orthop. (1978) 134:342–349.
Engkvist et al. Scan. J. Plast. Reconstr. Surg. (1979) 13:361–369.
Yannas Am. Chem. Soc. (1979) 16:1–9.
Gross Oral Surgery (1980) 49:21–26.
Rubak Acta Orthop. Scan. (1982) 53:181–186.
Nyilas et al. Trans. Am. Soc. Artif. Intern. Organs. (1983).
Arnoczky et al. Arthroscopy (1985) 1:247.
Webber et al. J. Ortho. Res. (1985) 3(1):36.

*Primary Examiner*—David Isabella
*Attorney, Agent, or Firm*—Lappin & Kusmer

[57] ABSTRACT

A prosthetic, resorbable articular cartilage and methods of its fabrication and insertion are disclosed. The prosthetic articular cartilage, when implanted in a humanoid joint, acts as a resorbable scaffold for ingrowth of native articular chondrocytes and supports natural articulating joint forces. The prosthetic articular cartilage is a dry, porous, volume matrix of biocompatible and bioresorbable fibers. These fibers include a natural polymer or analogs thereof, at least a portion of which may be crosslinked. The matrix is adapted to have an in vivo outer surface contour substantially the same as that of natural articular cartilage in an articulating joint, and has a pore size in the approximate range of about 100 microns to about 400 microns.

27 Claims, 6 Drawing Sheets

U.S. PATENT DOCUMENTS

| | | | |
|---|---|---|---|
| 4,505,266 | 3/1985 | Yannas et al. | 128/1 R |
| 4,542,539 | 9/1985 | Rowe et al. | 623/16 |
| 4,544,516 | 10/1985 | Hughes et al. | 264/108 |
| 4,578,079 | 3/1986 | Ruoslahti et al. | 623/11 |
| 4,589,881 | 5/1986 | Pierschbacher et al. | 623/11 |
| 4,614,794 | 9/1986 | Easton et al. | 530/356 |
| 4,620,327 | 11/1986 | Caplan et al. | 632/10 |
| 4,627,853 | 12/1986 | Campbell et al. | 623/16 |
| 4,642,120 | 2/1987 | Neve et al. | 623/16 |
| 4,787,900 | 11/1988 | Yannas . | |
| 4,801,299 | 1/1989 | Brendel et al. | 623/1 |
| 4,837,285 | 6/1989 | Beng et al. | 530/356 |
| 4,846,835 | 7/1989 | Grande | 623/11 |
| 4,880,429 | 11/1989 | Stone | 623/16 |
| 4,963,146 | 10/1990 | Li | 606/152 |
| 5,002,583 | 3/1991 | Pitaru et al. | 623/66 |
| 5,007,934 | 4/1991 | Stone | 623/20 |
| 5,108,438 | 4/1992 | Stone | 623/17 |
| 5,116,374 | 5/1992 | Stone | 623/16 |

PROSTHETIC ARTICULAR CARTILAGE

CROSS-REFERENCE TO RELATED APPLICATION

This application is a continuation-in-part of applicant's application Ser. No. 520,027, entitled "PROSTHETIC INTERVERTEBRAL DISC", filed May 7, 1990, which is a continuation-in-part application of Ser. No. 317,951, entitled "PROSTHETIC MENISCUS", filed Mar. 2, 1989 (now U.S. Pat. No. 5,007,934), which is a continuation-in-part application of Ser. No. 075,352, entitled "PROSTHETIC MENISCUS", filed Jul. 20, 1987 (now U.S. Pat. No. 4,880,429).

BACKGROUND OF THE INVENTION

The present invention relates to implantable medical devices. More particularly, this invention is directed to medical devices useful as prosthetic articular cartilage and in vivo scaffolds for regeneration of articular cartilagenous tissue, and to methods for fabricating such devices.

Articular cartilage covers the ends of all bones that form articulating joints in humans and animals. The cartilage acts in the joint as a mechanism for force distribution and as a lubricant in the area of contact between the bones. Without articular cartilage, stress concentration and friction would occur to the degree that the joint would not permit ease of motion. Loss of the articular cartilage usually leads to painful arthritis and decreased joint motion.

It is known that chondrocytes, the cells that produce articular cartilage, have the ability to migrate into a defect filled with a fibrin clot and form tissue substantially similar to natural cartilage (Arnoczky et al. (1985) *Arthroscopy* 1:247). Additionally, it has been shown that chondrocytes in tissue culture are capable of cell division and matrix synthesis (Webber et al. (1985) *J. Ortho. Res.* 3(1):36). However, the amount of cartilage formed by these procedures is generally not adequate to replace severely damaged joint surfaces in vivo.

Prior art treatment of injured or diseased cartilage has generally been both by attempts at surgical repair, replacement, or by excision. With repair or excision, regeneration of tissue may occur, although the tissue is usually temporary and inadequate to withstand the normal joint forces.

Replacement of articular cartilage usually has been by allografting (Sengupta et al. (1974) *J. Bone Surg.* 56B(1):167-177; Rodrigo et al. (1978) *Clin Orthoo.* 134:342-349) by periosteal grafts (see, e.g., Engkvist (1979) *Scan. J. Plast. Reconstr. Surg.* 13:361-369; Rubak (1982) *Acta Orthop. Scan.* 53:181-186) or with metal and/or plastic components (Rubash et al., eds. (1991) *Clin. Orth. Rel. Res.* 271:2-96). Allografting dead cartilage tissue has been tried for years with minimal success. This approach has been only partially successful over the long term due to the host's immunologic response to the graft, failures in the cryopreservation process, and failures of the attachment sites. Replacement of an entire joint surface with metal and plastic components has met excellent success for the older, more sedentary patients, but is generally considered insufficient for tolerating the impact of athletic activities, and has not been shown to restore normal joint mechanics.

In alternative prior art approaches, articular cartilage has been replaced with prostheses composed of bone and/or artificial materials. For example, U.S. Pat. No. 4,627,853 describes the utilization of demineralized allogenic or xenogenic bone segments as replacements. The proper functioning of these replacements depends on the differential demineralization of the bone segments. U.S. Pat. No. 3,551,560 describes a process of reconstructing cartilage including the use of a gel prepared from a colloidal solution of human or animal for treating implants with soluble bone protein to stimulate new cartilage. U.S. Pat. No. 4,846,835 describes a grafting technique for transplantation of chondrocytes to promote healing of lesions in articular cartilage. U.S. Pat. No. 4,642,120 describes the use of gel-like compositions containing embryonal chondrocytes.

Despite these developments, the replacement of cartilage tissue with structures consisting of permanent artificial materials generally has been less than satisfactory, principally because the opposing articular cartilage of human and animal joints is so fragile. The articular cartilage in the joints will not withstand abrasive interfaces nor compliance variances from normal which eventually result from the implantation of prior art artificial cartilage. Additionally, joint forces are multiples of body weight which, in the case of the knee and hip, are typically encountered over a million cycles per year. Thus far, prior art permanent artificial cartilage have not been composed of materials having natural articular cartilage properties, nor have they been able to be positioned securely enough to withstand such routine forces.

Repair of other tissues such as skin and nerve has been attempted using both synthetic and natural materials. For example, endodermal implants and artificial epidermis have been fashioned out of natural collagen and glycosaminoglycans (U.S. Pat. No. 4,060,081). Synthetic resorbable polyesters have been used for peripheral nerve regeneration applications (Nyiles et al. (1983) (*Trans. Am. Soc. Artif. Intern. Organs* 29:307-312), and collagen conduits have been used as a scaffold for nerve regeneration (U.S. Pat. No. 4,963,146).

Despite the availability of the foregoing technologies, a structure suitable as a prosthetic articular cartilage and constructed from natural resorbable materials, or analogs thereof, has not been developed. Thus, what is needed is an improved prosthetic scaffold for articular cartilage which is biocompatible, soft, lubricating, and durable.

Accordingly, it is an object of this invention to provide an improved articular cartilage prosthesis which allows for normal joint motion, is biomechanically able to withstand normal joint forces, and functions at those loads to protect the surrounding cartilage.

Another object is to provide a resorbable prosthesis which acts as a temporary in vivo scaffold for articular chondrocyte infiltration and cartilage regeneration.

Yet another object is to provide an articular cartilage prosthesis which is composed of biocompatible materials having an organization similar to that of the normal articular cartilage.

Still another object is to provide an articular cartilage prosthesis which is adapted for implantation by standard operative techniques.

A further object is to provide a method of regenerating articular cartilage tissue in vivo.

Another object is to provide a method by which such prosthetic articular cartilage scaffolds can be fabricated.

SUMMARY OF THE INVENTION

The present invention provides a biocompatible and at least partially bioresorbable structure for implantation into articulating joints, which assumes the form and role of articular cartilage. This prosthetic cartilage device also provides a scaffold for the regeneration of tissue having the physical characteristics of natural articular cartilage. Such a prosthesis can be implanted into any joint having articulating surfaces.

The prosthetic articular cartilage device of the present invention includes a dry, porous volume matrix adapted to have an in vivo outer shape contour substantially the same as that of natural articular cartilage found at the end of the long bones. The matrix has a pore size in the range of about 100 microns to about 400 microns. This matrix establishes a bioresorbable scaffold adapted for the ingrowth of articular chondrocytes and supports natural articulating joint load forces. In a Preferred embodiment of the invention, the matrix has a cylindrical shape.

The matrix is composed of biocompatible and bioresorbable fibers, a portion of which may be crosslinked. The fibers include a natural polymer, or an analog of a natural polymer such as a biosynthetic analog. In one preferred embodiment of the invention, the fibers of the matrix are polymers of natural molecules such as those obtained from animal or human tissue. Some Preferred natural fibers useful for the same purpose include collagen, elastin, and reticulin.

In some forms of the invention, the fibers are randomly orientated throughout the matrix, or are ordered at specified regions of the matrix. In other forms, the fibers assume substantially circumferentially-extending or substantially radially-extending orientations throughout the matrix.

The preferred matrix may also include polysaccharide molecules interspersed with the fibers. In preferred aspects of the invention, polysaccharides such as chondroitin 4-sulfate, chondroitin 6-sulfate, keratan sulfate, dermatan sulfate, heparan sulfate, heparin, hyaluronic acid, alginic acid, chitosan, and mixtures thereof are components of the matrix. These polysaccharides may be uniformly dispersed throughout the prosthetic cartilage, or may be concentrated in different regions of the matrix structure.

In various forms of the invention, polysaccharides may directly participate in covalent crosslinking formation with the fibers, or may interact with the fibers mechanically in the form of entanglement or through interlocking mechanisms, forming stable fiber-polysaccharide complexes.

The matrix may include about 75 to 100% by dry weight natural and/or synthetic fibers, and about 0 to 25% by dry weight, polysaccharides, the proportions of which may be constant throughout the structure or may be variable.

In a preferred embodiment of the invention, the matrix has a density of about 0.07 to 0.50 g matrix/cm$^3$ where "g matrix/cm$^3$" is a unit connoting the number of grams in a cubic centimeter of the matrix. In addition, the matrix may have an interfibrillary and intrafibrillary space of about 2 to 14 cm$^3$/g matrix.

In some embodiments of the invention, the matrix has a before-implantation shape of a right circular cylinder. A generally conical, biocompatible base component extends away from one base of the matrix for use in insertion and anchoring of the matrix to an underlying bone. This base component may be nonresorbable, partially resorbable, or totally resorbable. In the preferred form, the outer surface of the base component includes transverse circumferential ridges, or helical thread pattern providing a saw-tooth contour to cross-sections of the base component.

The invention also includes a method of regenerating cartilage tissue in vivo. This method includes providing the prosthetic articular cartilage device described above, and implanting it into a joint by surgical procedures, the prosthetic articular cartilage device assuming the shape of native articular cartilage of the joint into which it has been implanted.

Further, the invention includes a method for fabricating a prosthetic articular cartilage device of the type described above. Generally, the method includes placing a plurality of fibers and/or fibers and polysaccharides into a mold having a shape useful for joint function, contacting the polysaccharides and/or fibers with a chemical crosslinking reagent such that the fibers then assume the shape of the mold, and lyophilizing the resulting structure to obtain a dry, porous, volume matrix.

The fibers may be laid down in a circumferential orientation by rotating the mold as they are placed therein. Alternatively the fibers in the mold may be compressed with a rotating piston. Radial orientation of the fibers may be produced by manually painting the fibers in a linear, radially directed fashion.

Specific densities and pore sizes may be obtained in various regions of the matrix by compressing the fibers or the combination of fibers and polysaccharides in the mold subsequent to the chemical crosslinking step. This may be accomplished by applying pressure to a specific region of the matrix with a piston of a predetermined shape.

In a preferred aspect of the invention, the crosslinking step is performed using chemical agents which form intramolecular and intermolecular crosslinks. Useful chemical agents include, for example, glutaraldehyde, formaldehyde, biocompatible bifunctional aldehydes, carbodiimides, hexamethylene diisocyanate, bis-imidates, glyoxal, polyglycerol polyglycidyl ether, glyoxal, and mixtures thereof. Particularly useful crosslinking agents are 1-ethyl, 3-(3-dimethylaminopropyl) carbodiimide, polyglycerol polyglycidyl ether, formaldehyde and glutaraldehyde.

In other aspects of the invention, an additional crosslinking step is performed by subjecting it to dehydrothermal crosslinking procedures under heat and vacuum.

The invention will next be described in connection with certain illustrated embodiments. However, it should be clear that various modifications, additions, and deletions can be made without departing from the spirit or scope of the invention.

BRIEF DESCRIPTION OF THE FIGURES

The foregoing and other objects of this invention, the various features thereof, as well as the invention, itself, may be more fully understood from the following description, when read together with the accompanying drawings in which.

DESCRIPTION OF THE INVENTION

It has been discovered that prosthetic articular cartilage fabricated from biocompatible and bioresorbable fibers can be surgically implanted into a human joint so as to provide normal joint motion and strength. This prosthetic articular cartilage also acts as a scaffold for regenerating articular cartilage tissue whose ingrowth is encouraged by the physical characteristics of the implanted device. Such a prosthesis can be implanted into any joint having articulating surfaces, including but not limited to the knee, shoulder, elbow, and hip joints.

Figure 1:
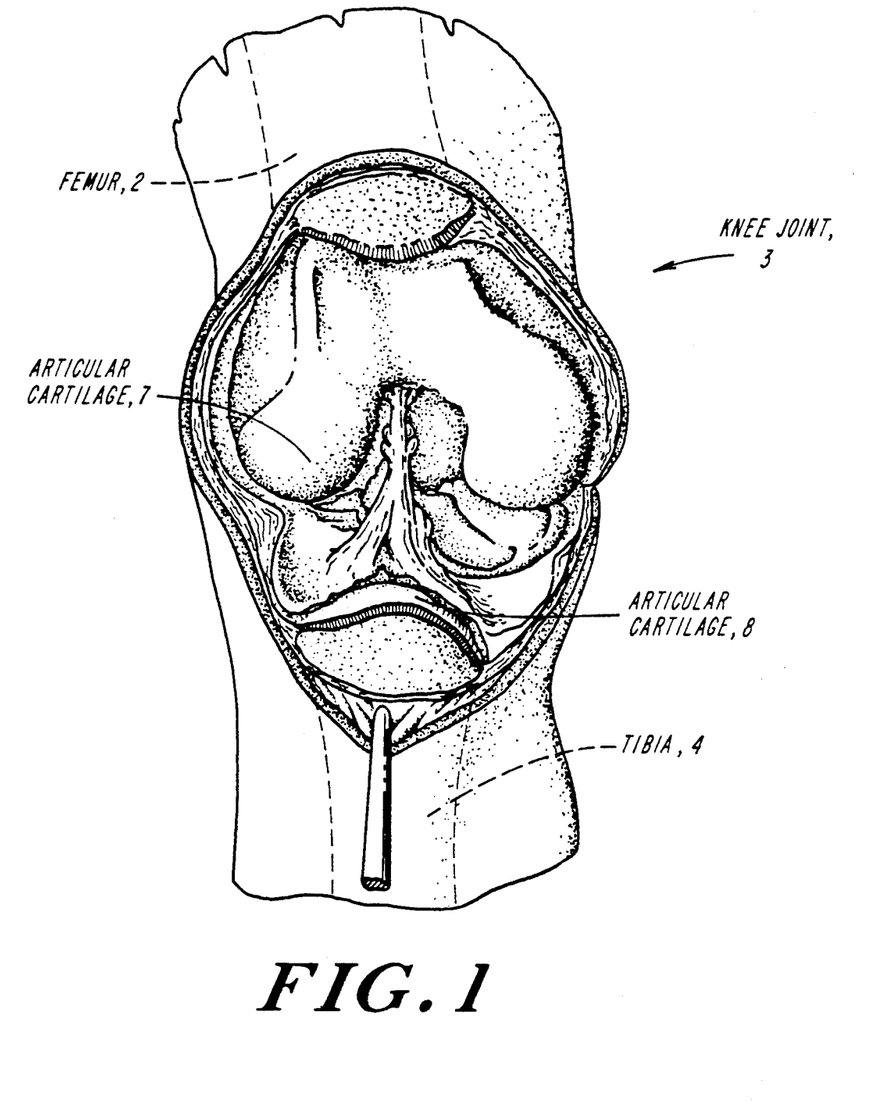
FIG. 1 shows a diagrammatic representation of a human knee joint, showing the location of the articular cartilage.

FIG. 1 is a diagrammatic representation of human knee joint 3 showing the normal positioning of articular cartilage 7 on the articulating end of femur 2 and articular cartilage 8 on the articulating end of tibia 4.

Figure 2:
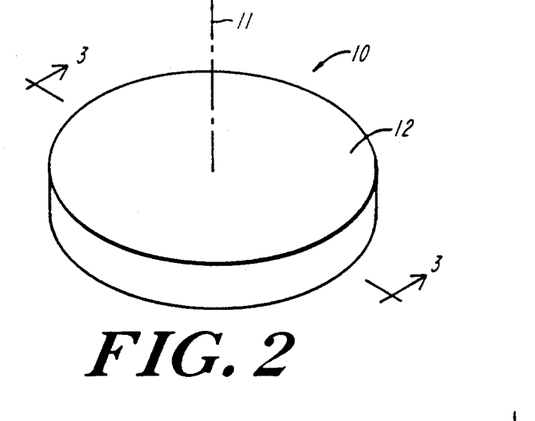
FIG. 2 shows a perspective view of one embodiment of the prosthetic articular cartilage of the present invention.
Figure 3:
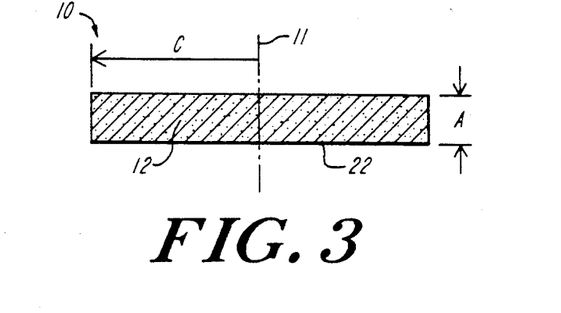
FIG. 3 shows a sectional view along line 3—3 of the prosthetic articular cartilage of FIG. 2.

A preferred form of a prosthetic articular cartilage device 10 embodying the invention is shown in FIG. 2. The device 10 includes a dry porous volume matrix 12 of biocompatible and at least partially resorbable fibers in the pre-implantation form of uniform height (A) right circular cylinder (radius C) extending fully about a central axis 11. FIG. 3 shows a sectional view along line 3—3 of the prosthetic articular cartilage device shown in FIG. 2. Other shapes (e.g., oval cross-section and/or non-uniform height) may be used for different embodiments. Device 10 is held in place on the bone, for example, with a biological glue such as bone cement, sea muscle glue, or fibrin glue.

Figure 4A:
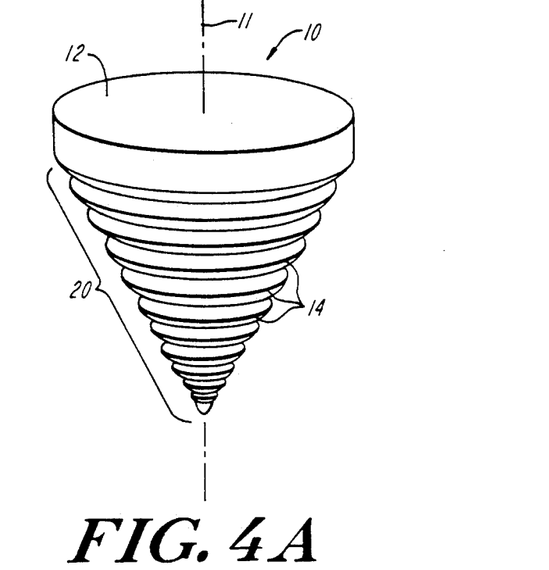
FIG. 4A shows a perspective view of an alternative prosthetic articular cartilage including a rigid ridged base component.

FIG. 4A shows an alternative embodiment in which a prosthetic articular cartilage device 10 includes a matrix 12 similar to that shown in FIGS. 1 and 2, and further includes a generally conical, rigid base component 20 which extends downward from the underside of matrix 12. Base component 20 shown in FIGS. 4A and 4B has a textured, ridged, or otherwise non-smooth lateral surface. In these figures, elements corresponding to similar elements in FIG. 2 are identified with identical reference designations. Base component 20 is adapted for insertion into a pilot hole into cancellous bone, and permits impaction and anchoring of device 10 into that bone.

Figure 4B:
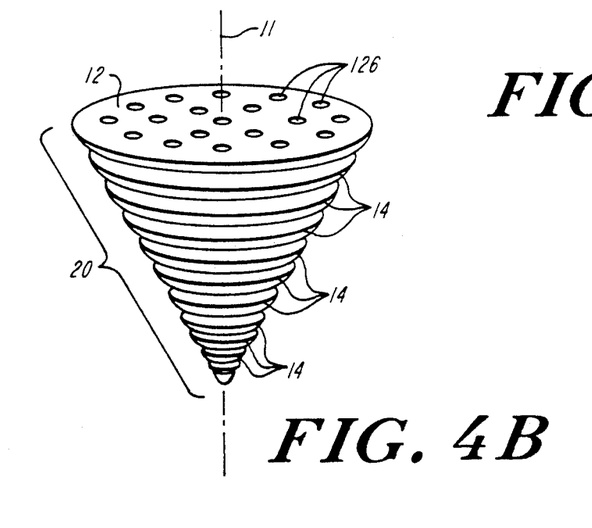
FIG. 4B shows a perspective view of the rigid ridged base component.

In the embodiment of FIGS. 4A and 4B the base component 20 includes a plurality of concentric (about axis 11) ridges 14 on its outer surface. In other embodiments, different forms of roughness (including a self-tapping helical thread, for example) may be established on the lateral surface of base component 20. Ridges 14 of base component 20 secure immediate fixation (by friction) and impaction into the bone, permitting the softer matrix 12 to remain flush with the surface of the surrounding area existing articular cartilage of the bone into which the prosthetic devise 12 is being implanted. Base component 20 may function in this supportive capacity until sufficient tissue ingrowth occurs in the matrix 12 to then provide that function.

The matrix 12 of the prosthetic articular cartilage device may be fabricated of any biocompatible, bioresorbable fibers which include a natural material or a biosynthetic or synthetic analog thereof. These fibers are preferably polymeric in structure, and can provide mechanical strength and protection and lubrication while encouraging tissue ingrowth. Useful fibers include collagen, reticulin, elastin, cellulose, alginic acid, chitosan, or synthetic and biosynthetic analogs thereof.

Particularly useful fibers include type I and type II collagen. The type I collagen molecule is a triple helix. It has a unique protein configuration that is a coiled coil of three polypeptide chains or alpha chains. Two of the alpha chains are identical and are called alpha 1 chains. The third chain is slightly different in amino acid composition and is called the alpha 2 chain. Each alpha chain twists in a left-handed helix with three residues per turn. Three chains are wound together in a right-handed superhelix to form a rod-like molecule about 1.4 nanometer in diameter and 300 nanometers in length. The alpha chains each contain about 1,050 amino acid residues The molecular weight of a type I collagen molecule is about 300,000 daltons (300 kD). Every third amino acid residue within each alpha chain within the triple helix is a glycine residue.

Collagen is characterized by a high content of proline and hydroxyproline residues, the absence of tryptophan, a minor amount of aromatic amino acid, and a significant amount of dicarboxylic and dibasic amino residues. At both ends of the collagen molecule there are terminal peptide sequences known as telopeptides which are globular, in structure, and which lack glycine at every third residue. These telopeptides are the primary sites of intermolecular crosslinking in the molecule.

Type 11 collagen is also a triple-stranded helix of amino acids. It has more hydroxyproline and hydroxylysine than does type I collagen, and is unique in that all three strands are identical alpha chains.

In the matrix of devices of the invention, the fibers may be ordered in substantially circumferentially-extending or substantially radially-extending orientations, with the density of fibers being substantially uniform throughout the matrix. Alternatively, the matrix fibers may be unordered. In either the ordered or unordered configuration, the density of the fibers may be non-uniform. In the non-uniform configuration, relatively high densities of fibers may be established at anticipated points of high stress by local application.

In an alternative aspect of the invention, the intrafibrillary and interfibrillary space is relatively high, a condition which promotes ingrowth of regenerated cartilage tissue. For example, the density of the cartilage may be in the range of about 0.07 to 0.25 gram matrix/cm$^3$. Alternatively, the intrafibrillar and interfibrillar space may be relatively low, a condition which provides cushioning, lubrication, and mechanical support for the knee joint and which retards tissue and cell ingrowth, thereby diminishing the rate of scaffold resorption (e.g., density is in the range of about 0.25 to 0.50 g matrix/cm$^3$.

Polysaccharides may be dispersed throughout the fibers. Alternatively, they may act as intermolecular crosslinks between fibers. These polysaccharide crosslinks are composed typically of at least one of the group of molecules consisting of chondroitin 4-sulfate, chondroitin 6-sulfate, keratan sulfate, dermatan sulfate, heparan sulfate, heparin, hyaluronic acid, alginic acid, and chitosan. Native articular cartilage has polysaccharide composed mainly of three principle types; chondroitin 4-sulfate, chondroitin 6-sulfate, and keratan sulfate. Hyaluronic acid is also present in smaller quantities. The dispersion of polysaccharide crosslinks is preferably uniform, but may be more concentrated at anticipated points of high stress. In such configurations, the polysaccharide concentration may be in the range of about 10 to 25% in the high stress areas, and in the range of about 0 to 10% in the lower stress areas. However, when uniform, the dispersion of polysaccharide throughout the prosthetic articular cartilage may be, for example, in the range of about 1 to 25%.

The temporary stability of the shape of the structure when in vivo, and the rate of cartilage resorption, are both attributed to the effective crosslinking formation between at least one portion of the fibers. The crosslinking reagents used may be any biocompatible bifunctional reagents which interacts with amino carboxyl, or hydroxyl groups resulting in covalent bond formation between adjacent molecules (intermolecular crosslinks). Useful crosslinking reagents include aldehydes, hexamethylene diisocyanate, bis-imidates, polyglycerol polyglycidyl ether, and carbodiimides.

Alternatively, intermolecular crosslinkages can be established through a dehydrothermal process (heat and vacuum) which results in peptide bond formation between an epsilon amino group of lysine or hydroxylysine and a carboxyl group of aspartic or glutamic acid, an ether bond formation between two hydroxyl groups, or an ester bond formation between a carboxyl and a hydroxyl group.

The crosslinked device maintains a sufficient degree of hydrophilicity and elasticity which simulates the properties of the natural cartilage, i.e., ability to sustain mechanical stress and to protect and lubricate articular surfaces. In addition, the structure provides an ideal environment for cell infiltration and extracellular matrix synthesis and deposition resulting in regeneration of natural cartilage tissue.

The crosslinked device has a relatively high thermal stability between about 55°-85° C., preferably between about 60°-75° C., for sufficient in vivo stability. This may be achieved through manipulation of the crosslinking conditions, including reagent concentration, temperature, pH, and time.

In alternative forms of the invention the densities of collagen and distribution of polysaccharide molecules and crosslinks may be varied, permitting accommodation of differing stress levels, rates of ingrowth, and resiliency. Differing densities may be obtained in vivo where a device having uniform density is implanted, and body loading causes non-uniform compression of the device.

In one embodiment, the prosthetic articular cartilage device is constructed mainly of type II collagen matrix with polysaccharide molecules and type I collagen fibers reinforcing the matrix. Alternatively, the device is constructed mainly of type I collagen with polysaccharides and type II collagen fibers reinforcing the matrix.

The collagen fibers required to fabricate such a prosthetic articular cartilage can be obtained as follows. Type I collagen may be prepared from the Achilles tendons of mammals. Type II collagen matrix may be obtained from the articular surfaces of the joints of animals. The tissues are treated with a series of mechanical and chemical means to either totally remove the non-collagenous materials or reduce them to a minimal level. In the preferred processing steps, the joint surface and tendons are separated and mechanically disintegrated into fine pieces useful for further processing. The disintegration may be achieved by grinding the tissue at liquid nitrogen temperature, or by cutting the tissue into small pieces with a sharp knife.

More specifically, to obtain type I collagen, tendon from bovine, porcine, or sheep is cleaned of fascia and extraneous tissues and minced. The minced tendon is first extracted in a salt solution at neutral PH. Salt extraction of cartilage at neutral pH removes a small portion of the collagen molecules that are newly synthesized and have not yet been incorporated into the stable fibrils. Salt also removes some glycoproteins and proteoglycans that are associated with collagen through electrostatic interactions. Useful salt solutions contain NaCl, KCl, and the like.

Lipids that are associated with the cell membranes or collagenous matrices may be removed by first extracting with detergents such as Triton X-100, followed by extracting with ether-ethanol mixtures. The concentration of Triton X-100 is usually about 2 to 4%, but is preferably about 3%. The preferred mixture of ether-ethanol is usually at about a 1:1 ratio (v/v). The period of extraction is usually from 8 hours to 96 hours, and is preferably from about 24 to 48 hours.

Further extraction may be accomplished by matrix swelling conducted at two extreme pHs. Both acidic and basic swelling weakens the non-covalent intermolecular interactions, thus facilitating the release of non-covalently attached glycoproteins, proteoglycans, and other non-collagenous molecules through the open pores of the collagenous matrices.

The swelling of matrix at alkaline pH is done by treating the collagen at a pH above 13 with Ca(OH)$_2$, NaOH, or the like, for a period of about 8-96 hours. Alkali extraction in the presence of triple-helical stabilizing salts such as (C$_3$)$_4$NCl, (NH$_4$)$_2$SO$_4$, or the like, reduces the potential risk of denaturation of the collagen. Alkali treatment dissociates the non-crosslinked glycoproteins and proteoglycans from the collagen matrices. The alkali also removes the residual lipids through saponification.

The acid swelling may be conducted at a pH below 3 in the presence of acetic acid, HCl, or the like. Like the alkali treatment, the acid swelling removes non-crosslinked glycoproteins and proteoglycans.

The non-triple helical portions of the collagen molecule (telopeptides) are involved in intermolecular crosslinking formation. They are weak antigens and are susceptible to attack by proteases, such as pepsin, trypsin, and the like. Prolonged digestion with such proteases dissociates the fibrils (fibers) into individual molecules. However, if the digestion process is properly controlled such that maximal telopeptides are removed without complete dissociation, the immunogenic properties of the fibrils can be reduced to a minimal level without compromising the mechanical strength. For example, to isolate molecular collagen, the digestion of skin or tendon with pepsin is usually conducted at an enzyme:collagen ratio of about 1:10 for about 24 to 96 hours at below room temperature. In comparison, fibrils may be obtained by limited pepsin digestion achieved at a ratio of about 1:100 (enzyme:collagen) for about 24 to 96 hours at 4° C.

Type II collagen can be obtained from bovine, porcine, or sheep condylar or patellar cartilage. The adhering tissues of the articular cartilage are scraped off with a knife and minced. The minced cartilage is extracted in a guanidine hydrochloride solution to remove the majority of the cartilage proteoglycans. After extensive rinsing with water, the type II collagen rich material is digested with pepsin in an acid solution at pH about 2-3 for 24 to 48 hours with shaking at 4° C. Both inorganic acids and organic acids may be used, including hydrochloric acid, phosphoric acid, lactic acid, acidic acid, and the like. The pepsin-solubilized collagen is purified by repeated precipitation and redissolution by methods well known in the art.

Collagen fibers obtained according to this methodology are then used to fabricate the prosthetic articular cartilage of the present invention. However, it must be appreciated that collagen obtained from other sources, such as biosynthetically-produced collagen or analogs thereof, and obtained by other methods, may also be used in the construction of the prosthetic articular cartilage.

Figure 8:
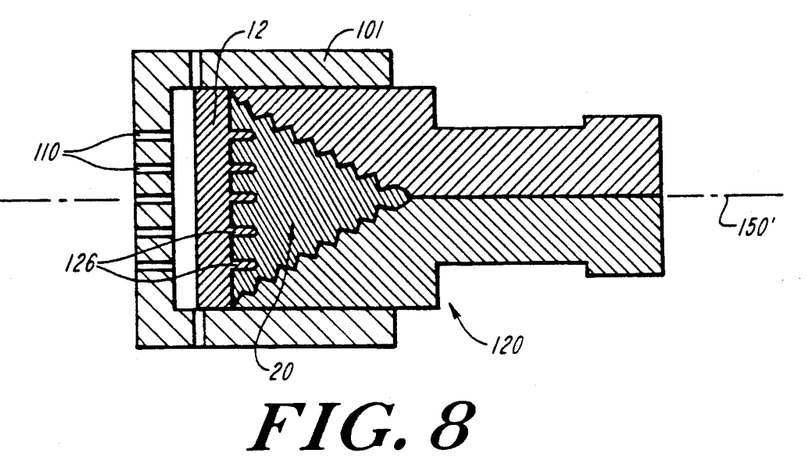
FIG. 8 shows the mold of FIG. 6 filled with the matrix-base component composite prosthetic articular cartilage.

The method of fabrication includes molding the collagen fibers into a predetermined shape using, for example, the mold forms described below in conjunction with FIGS. 5, 6, and 8. The fibers may be placed randomly in the mold, or may be oriented in specific directions to achieve a cartilage having specific structural characteristics. Other components such as polysaccharides which participate in the crosslinking reaction can be mixed in with the fibers in a random or non-random fashion before the structure is crosslinked. Various useful crosslinking Procedures include chemical and/or dehydrothermal methods.

The base component has a generally conical shape that extends away from one base of the matrix. It may have transverse circumferential ridges or a helical thread pattern as well. The component may be composed of a nonresorbable material such as titanium, stainless steel, or high molecular weight polyethylene which is machined to the desired proportions. Alternatively, the base component may be composed of partially or completely resorbable materials such as hydroxyapatite and collagen or tricalcium phosphate, respectively.

Figure 6:
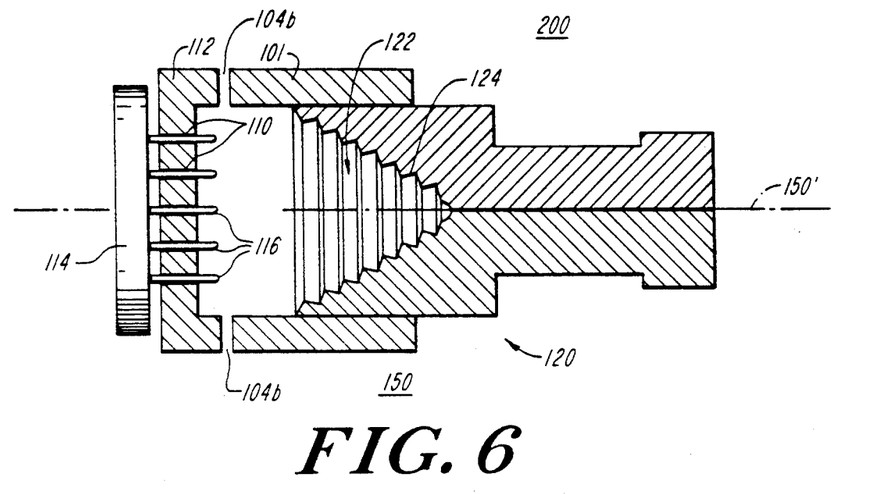
FIG. 6 shows a mold designed for the fabrication of a prosthetic cartilage having a cylindrical matrix attached to a substantially conical, rigid base component.

FIG. 6 shows a mold suitable for forming a base component 20 having a substantially conical shape with a top surface with an array of holes extending therein. The mold includes a cup-shaped piece 101 having an array of holes 110 at its base surface 112. A support member 114 supports an array of elongated metal pins 116 which are adapted to fit into the hole array 110 in cup shaped member 101. A two piece piston 120 is shown for sliding motion within the cup shaped member 101. The piston includes internal conical region 122 which has a rough surface texture on its inner surface 124. In the illustrated embodiment shown in FIG. 6, the rough surface has a saw tooth profile. Other rough surfaces may be used for other embodiments.

Figure 7:
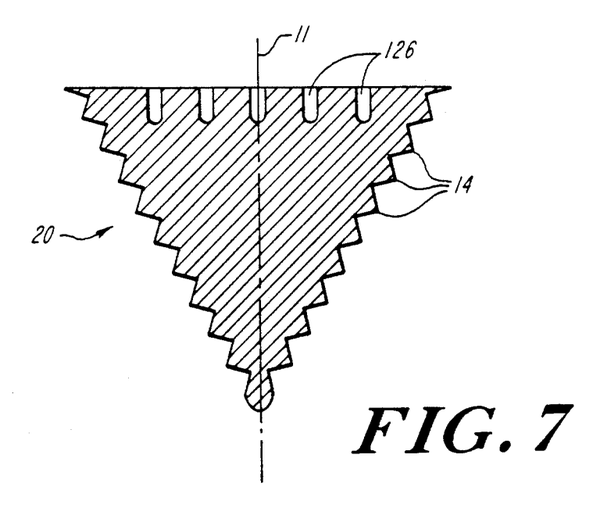
FIG. 7 is a cross-sectional view of the base component shown in FIB. 4B.

In operation, the material for the base component, a hydroxyapatite/collagen (80:20 by weight) mixture is inserted within the conical region 122 of the piston 120. The piston 120 is then driven against the pin array 116 extending through cup shaped member 101, thereby establishing a generally conical or base component having an array of holes 126 extending therein. This element is shown in FIG. 7. The array of holes can also be seen in FIG. 4B. FIG. 8 shows the piston 120 without the support member 114 and pin array 116, so that the holes 110 in the base component 20 are empty.

Figure 9:
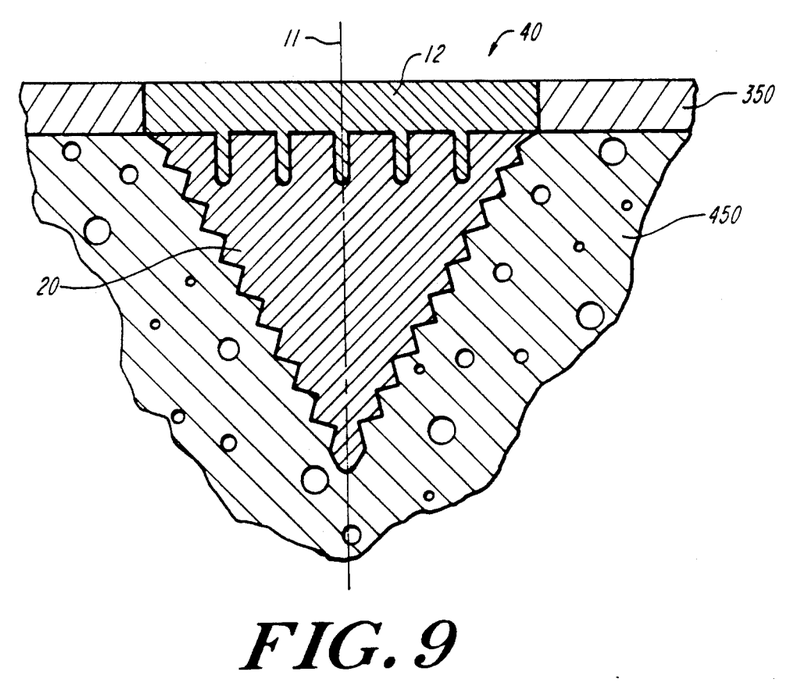
FIG. 9 is a diagrammatic cross-sectional representation of the composite matrix-base component prosthetic articular cartilage device in place in a joint.

Upon establishing the conical base component, it is removed from the piston 120, and the fibers for forming the matrix are painted on the top of the conical base component 20 as it sits in the piston 120. Thereupon, the piston 120 is driven toward the hole array 110 in the cup shaped member 101 so that the fibers painted on the top surface of the base component 20 are compressed. As the compression occurs, some of the fibers are forced into the holes 126 in the top of the base component. Following compression, the composite element 40 formed by the base component 20 and matrix 12 is removed from the piston 120 and dried in the manner set forth in connection with EXAMPLES 6 or 7, below. The resultant matrix 12 as connected to the base component 20 is shown in FIG. 9.

The base component alternatively may be constructed by filling a nylon mesh having a conical form with an hydroxyapatite/collagen (20:80 by weight) slurry, and then letting it dry. The surface of the hardened component may then be scored to provide a friction surface.

When a partially or totally resorbable base component is positioned into a hole drilled into or otherwise made in cancellous bone, bone forming cells may migrate into the component and synthesize bone. With time, the resorbable base component or a resorbable portion thereof is resorbed, leaving the newly formed bone as an anchor for the device.

By following the processes described in the examples set forth below, prosthetic articular cartilage of the form shown in FIGS. 2, 7, or 9 may be constructed having the characteristics listed below in TABLE 1.

TABLE 1

| I. PHYSICAL CHARACTERISTICS |
|---|
| A. Matrix (pre-implantation cylinder) |
| height A = 3.0–6.0 mm |
| radius C = 1.0–5.0 cm |
| density = 0.07–0.5 g/cm$^3$ |
| intra- and interfibrillary space = 2–14 cm$^3$/g matrix |
| pore size = 100–400 μm |
| B. Base Component (conical) |
| Maximum radius of base = 1.0–5.0 cm |
| height = 1.0–6.0 cm |
| II. COMPOSITION |
| A. Matrix |
| 1. collagen fiber content = 75–100% dry wt. |
| 2. polysaccharide content = 0–25% |
| chondroitin 4-sulfate = 0–7.5% |
| chondroitin 6-sulfate = 0–7.5% |
| keratosulfate = 0–5% |
| hyaluronic acid = 0–5% |
| B. Base Component |
| 1. calcium phosphate ceramic = 80–95% (tricalcium phosphate or hydroxyapatite) |

TABLE 1-continued 2. collagen = 5-20%

The following non-limiting examples describe methods of fabrication and in vivo testing of the prosthetic articular cartilage of the invention.

EXAMPLE 1

Preparation of Purified Type I Collagen

A) Tissue:

Bovine, porcine, or sheep Achilles tendon is obtained from USDA-approved slaughter houses. The preferred age of the animals is between 12-18 months. The tissue is kept cold during the purification process except where specified to minimize bacterial contamination and tissue degradation.

B) Mechanical Disintegration:

The adhering tissues of carefully selected tendons are first scraped off mechanically. The tendons are then minced or cut into fine pieces and washed in excess quantities (10 volumes) of cold water to remove residual blood proteins and water soluble materials.

C) Salt Extraction:

The washed tendons are extracted in ten volumes of 5% NaCl, 0.01M Tris, pH 7.4, for 24 (+/−volumes 4) hours to remove salt soluble materials. The salt extracted tendons are repeatedly washed in about 10 volumes of water to remove the salt.

D) Lipid Extraction:

The material is extracted in 3% Triton X-100 for 24 (+/−2) hours. The detergent is removed by extensive washing with water. The material is then extracted in 3-4 volumes of ether-ethanol (1:1 vol/vol) for 24 (+/−2) hours to further minimize the lipid content. The lipid extracted material is extensively washed in water to remove the ether and ethanol.

E) Matrix Swelling:

The material is then subjected to two extreme pH extractions to remove non-collagenous materials. Alkaline extraction is conducted with 3-4 volumes of 0.5M NaOH at pH 13.0-14.0 at room temperature (RT) in the presence of 1.0M $Na_2SO_4$ for 24 (+/−2) hours with mild agitation.

Following alkaline extraction, the pH is neutralized with HCl and the material is washed with water. The pH is then adjusted to 2.5-3.0 by adding concentrated acetic acid to a final concentration of 0.5M. The acid extraction is continued for 24 (+/−2) hours with agitation.

F) Limited Proteolytic Digestion:

The acid swollen tendon is then subjected to a limited proteolytic digestion with pepsin (enzyme:collagen =1 : 100) for 24 (+/−) 2 hours at 4° C. The pepsin and telopeptides are removed through dialysis.

The swollen fibrillar material is then coacervated by adjusting the pH to its isoionic point with 1M NaOH or HCl or by adjusting the ionic strength to 0.7M with NaCl. The aggregated collagen fibers are harvested by filtration, and the filtered material extensively washed with cold buffered solution The highly purified type I collagen may be stored wet at −20° to −40° C. or stored in a freeze dried form until used.

EXAMPLE 2

Preparation of Purified Type II Collagen

A) Tissue:

Bovine, porcine, or sheep condylar or patellar cartilage is obtained from USDA-approved slaughter houses. The preferred age of the animals is between 12-18 months. The tissue is kept cold during the purification process except where specified to minimize bacterial contamination and tissue degradation.

B) Mechanical Disintegration:

The adhering tissues of the articular cartilage are first scraped off mechanically and washed with water. The cartilage layers are removed with a sharp knife. The thin slices of the articular cartilage are further minced with a homogenizer to yield fine particles of less than 0.5 mm.

C) Guanidine Hydrochloride Extraction:

The homogenized fine particles of articular cartilage are extracted in 10 volumes of 4M guanidine hydrochloride ($GnCl_2$) for 24 (+/−2) hours at 4° C. with constant shaking. The extractant containing the proteoglycans and other non-collagenous materials is discarded.

D) Pepsin Digestion:

The type II collagen rich residues are extensively washed with water. The washed residues are then digested with pepsin (enzyme:cartilage collagen = 1:10 w/w) in 0.1M lactic acid at pH 2.5, 4° C. with constant shaking for 48 (+/−4) hours. The enzyme is inactivated by raising the pH to 7 with 1M NaOH. The pepsin solubilized collagen is collected by filtration. The filtrate which contains the soluble collagen is precipitated by adding NaCl to a concentration of 0.7M. The precipitated collagen is then collected by centrifugation and the supernatant is discarded. The precipitate is redissolved in 0.05M lactic acid and NaCl is again added to a 0.7M concentration at room temperature to precipitate the collagen. The precipitate is collected again by centrifugation. The redissolution and reprecipitation is performed for a total of three times as a means to purify the collagen. The final precipitated fibers are extensively washed with ethanol and kept frozen until use.

EXAMPLE 3

Mold Fabrication

A mold 100 useful for fabricating the prosthetic articular cartilage is made of implantable stainless steel or biocompatible plastics such as polytetrafluoroethylene (PTFE), polypropylene, polyacetyl resins, or a combination of these materials. The mold 100 is composed of a generally cup-shaped piece 101 and an associated compression piece 106 (or piston) as shown in FIG. 5.

Figure 5:
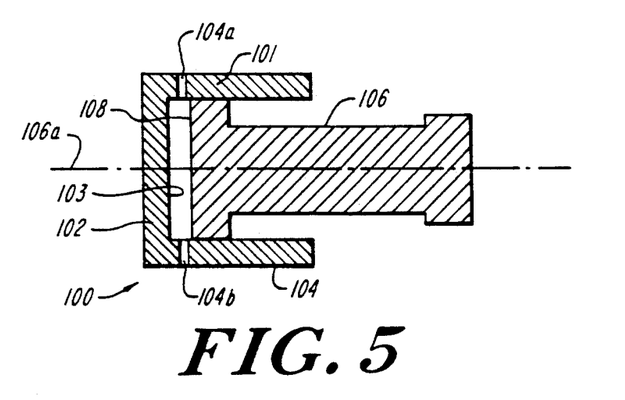
FIG. 5 shows, in section, a mold designed for the fabrication of a prosthetic articular cartilage having a cylindrically shaped matrix.

By way of example, for fabricating the pre-implantation cylindrical disk-shaped matrix illustrated in FIGS. 2 and 3, the mold 100 of FIG. 5 is used. The cup-shaped piece 101 has a disk-like base portion 102 with cylindrical sidewalls 104 extending therefrom with an inner diameter substantially equal to that of the desired prosthetic cartilage. The inner surface 103 of base portion 102 has the desired shape of one side of the matrix-to-be-formed. The sidewalls 104 have the form of a hollow cylinder which has the same inner diameter as the inner surface 103 of the cup-shaped piece 101. The side walls 104 include channels 104a and 104b which allow liquid to pass through under high pressure.

The compression piece 106 is a cylindrical piston which has an outer diameter slightly less than the inner diameter of sidewalls 104. The "top", or crown, surface 108 of piston 106 has the desired shape of one side of the matrix-to-be-formed.

During fabrication of the prosthetic articular cartilage device 10, the constituent fibers (in a fluid) are placed against the surface 103 of piece 102. Then the crown surface 108 of piston 106 is driven toward surface 103 along a compression axis 106a until the fibers are compressed, the fluid is driven out through channels 104a and 104b, and the desired axial dimension of the compressed fiber matrix attained. The mold is then frozen in preparation for chemical crosslinking.

EXAMPLE 4

Preparation of Totally Resorbable Base Component

A) The collagen content of the highly purified type I collagen fibers from EXAMPLE 1 or type II fibers from EXAMPLE 2 is determined either by gravimetric methods or by determining the hydroxyproline content assuming a 13.5% by weight of hydroxyproline is type I collagen. The amount of purified material needed to fabricate a cartilage device having a desired density is then determined and weighed.

B) The collagen fibers are re-dispersed in 0.01M HCl and homogenized to the collagen concentration in the dispersion of about 1%.

C) Tricalcium phosphate (TCP) particles (250 μm size) are mixed with the collagen dispersion (TCP:collagen =90:10 w/w). The collagen-TCP complex is then placed into a substantially conical-shaped mold region of a piston 120 in a mold form 150 (FIG. 6) having a substantially conical region 122. The piston 120 is a two piece element, so that following formation of a base component, the two pieces may be separated enabling removal of the saw-toothed (in this example) base component. The collagen-TCP complex in the conical region is then compressed, removed, and dried under a hood for 2 to 3 days. The mold form 150 includes an array of small stainless steel pins 116 of 0.5 mm in diameter that extend from a support member 114 2 to 10 mm in the direction of axis 150' into the interior conical space 122 of the interior void region of the mold. Following compression of the base component material in the mold, and drying of the resulting structure, the support member 114 is moved away from the mold form 150 so that the steel pins 116 are withdrawn from the base component 20. As a result, an array of small holes is established in the top of the base component 20 for the interdigitation of the articular collagen matrix with the base component 20, thereby securing the matrix to the base component 20, as described below in EXAMPLE 6.

EXAMPLE 5

Preparation of Partially Resorbable Base Component

A)-B) (Same as in EXAMPLE 4).

C) Hydroxyapatite (HA) particles (250 μm size) are mixed with the collagen dispersion from EXAMPLE 4B (HA:collagen =90:10 w/w). The collagen-HA complex is then molded into a substantially conical shaped mold form 150 (FIG. 6) and dried under a hood for 2-3 days similar to the base component of EXAMPLE 4.

D) (Same as in EXAMPLE 4).

EXAMPLE 6

Device I Fabrication

A)-B) (Same as in EXAMPLE 4).

C) The PH of the dispersion is slowly adjusted to pH 5 with 0.1M NaOH to coacervate the collagen fibers.

D) The coacervated collagen fibers are carefully fit into a mold of specified dimensions, e.g. according to the exemplary cartilage described above in conjunction with FIGS. 2-3 (see FIGS. 5 and 6 for the description of molds). Collagen fibers are laid down in random manner or in an oriented manner. In the oriented manner, circumferential orientation of the fibers is produced by rotation of the piston about its principal axis as the material is compressed in the mold; radial orientation is produced by manual painting of the collagen fibers in a linear, radially directed fashion.

E) The compressed fibers interdigitating with the delivery device are frozen at −20° C., to solidify the fibers and to facilitate the removal of the molded fiber from the mold.

F) The resulting structure is crosslinked by soaking in a 0.2% glutaraldehyde solution, pH 7.4, for 24 (+/−0.5) hours. Each glutaraldehyde-crosslinked cartilage device is subsequently rinsed repeatedly in 500 ml of phosphate buffered saline (PBS) solution, pH 7.4, for 4, 8, 24 and 48 hours.

G) The rinsed matrix is then lyophilized.

EXAMPLE 7

Device II Fabrication

A)-G) (Same as in EXAMPLE 6).

H) The lyophilized matrix is subjected to dehydrothermal crosslinking by vacuum and heat. The vacuum is first applied to reduce the residual water content to a minimal level (some structural water, about 3%, may still be associated with collagen triple-helix as part of the structure stabilizing factor). The heat is increased in steps to 110° C. (+/−5° C.), and continually applied at 110° C. under vacuum for 24 (+/−2) hours.

EXAMPLE 8

Device III Fabrication

A) (Same as in EXAMPLE 6).

B) The collagen material is dispersed in 0.01M HCl solution at pH 2-2.5. Predetermined amounts of various polysaccharides are weighed and dissolved in water. For example, for a given density of 0.25 g/cc, the collagen content will be 0.244 g, the hyaluronic acid content will be 0.003 g, and the chondroitin sulfate content will be 0.003 g for a 2.5% polysaccharide content. The polysaccharide solution is mixed in with the collagen and homogenized as in EXAMPLE 4.

C)-G) (Same as in EXAMPLE 6).

EXAMPLE 9

Device IV Fabrication

A)-E) (Same as in EXAMPLE 6).

F) The molded collagen is crosslinked in 5% polyglycerol polyglycidyl ether in 50% ethanol and 0.1M $Na_2CO_3$ at PH 10.0 for 24 (+/−2) hours. The crosslinked device is rinsed for 4, 8, 24 and 48 hours, each with 500 ml of PBS, pH 7.4.

G) (Same as in EXAMPLE 6).

EXAMPLE 10

Device V Fabrication

A)-E) (Same as in EXAMPLE 6).

F) The molded collagen is crosslinked in the presence of 1-ethyl-3-(3-dimethylaminopropyl) carbodiimide (10 mg/g matrix) in 0.9% NaCl, pH 4.7 at room temperature for 24 (+/−2) hours. The addition of carbodiimide is made every 3 to 4 hours, and the pH is adjusted to 4.7 after each addition of carbodiimide.

G) (Same as in EXAMPLE 6).

EXAMPLE 11

Device VI Fabrication

A) The collagen content of the highly purified type I and type II collagen from EXAMPLES 1 and 2 is determined either by gravimetric methods or by determining the hydroxyproline content assuming a 13.5% by weight of hydroxyproline is type I and type II collagens.

B) Type I and type II collagens are each dispersed and homogenized, followed by careful mixing of the two collagens to form a uniform dispersion containing type I and type II collagens.

C)-G) (Same as in EXAMPLE 6).

EXAMPLE 12

Device VII Fabrication

A)-C) (Same as in EXAMPLE 6).

D) The air dried base component 20 made in accordance with EXAMPLE 4 or EXAMPLE 5 is reinserted back to the mold form 200 (FIG. 6).

E) The coacervated collagen fibers are carefully fit into the mold on top of the saw toothed base. Collagen fibers are laid down in random manner or in an oriented manner.

F)-H) (Same as steps E-G in EXAMPLE 6).

EXAMPLE 13

Implantation Technique

A pilot hole is made in the center of the arthritic defect in a joint using standard open and/or arthroscopic surgical techniques involving, for example, an instrument having a conically shaped end with a diameter slightly smaller than the diameter of the base component. Loose cartilage and eburnated bone are debrided down to a bleeding bed of bone using a burr. A composite prosthetic articular cartilage device including a ridged base component with a collagen matrix surface is fitted to a metal inserter and tapped into place, down the pilot hole, obtaining a press fit. FIG. 9 shows the composite device in place in natural articular cartilage 350 and cancellous bone 450.

EXAMPLE 14

Testing

The prosthetic articular cartilage is evaluated in vivo using animal models and in vitro to determine ability to function or to serve as a regeneration template for normal cartilage tissues.

Figure 10A:
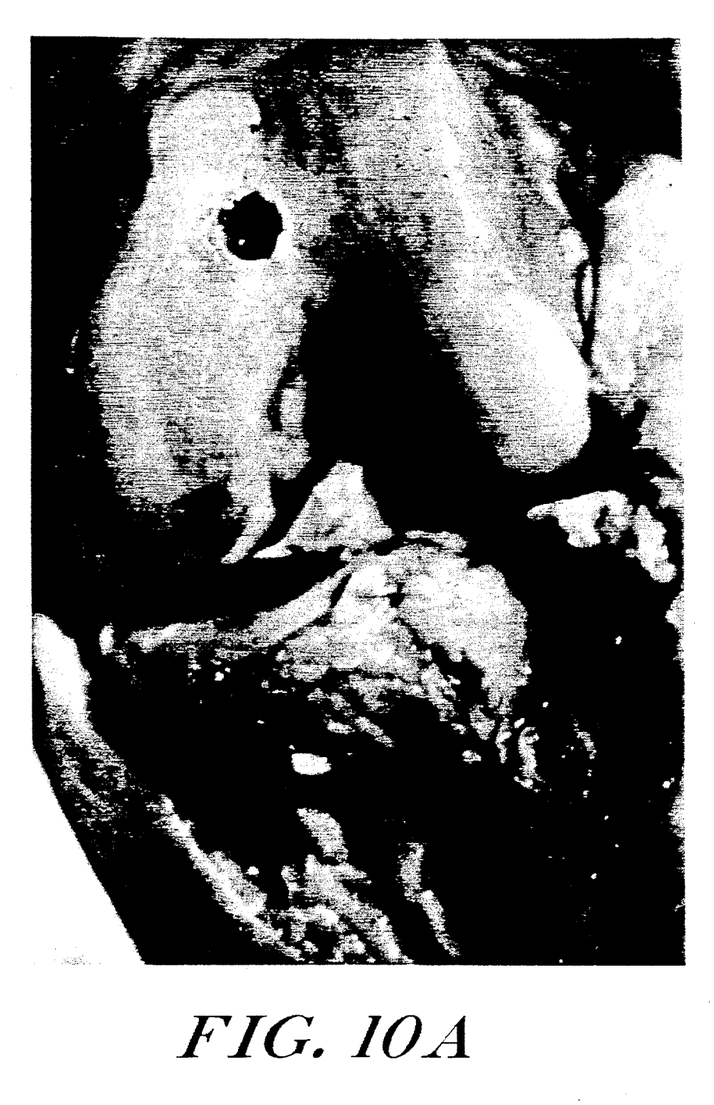
FIG. 10A is a photographic representation of a defect in the natural articular cartilage of a human knee joint.
Figure 10B:
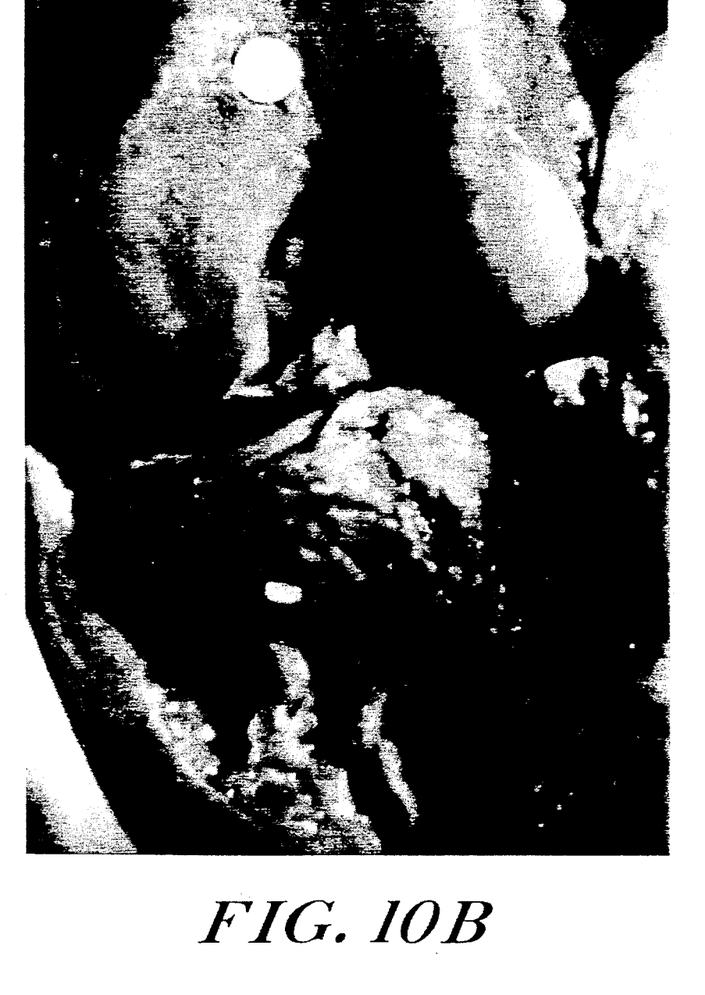
FIG. 10B is a photographic representation of the prosthetic articular cartilage placed in a human knee joint.

1. In vivo Testing:

Full thickness articular cartilage defects are created by a hand trephine measuring 5 mm in diameter by 5 mm in-depth in the media and lateral femoral condyle of mature dogs. FIG. 10A shows a similar defect in the human knee joint. In randomized fashion either the medial or lateral defect is filled with the prosthetic articular cartilage device described above. FIG. 10B shows a similar filled human knee defect. The joints are then harvested at three and six months. The tissues are processed with standard histologic stains to evaluate the quality of the regenerated tissue, and the presence of type II collagen, chondroitin-4-sulfate, chondroitin-6-sulfate and keratan sulfate.

2. In vitro Testing:

Articular chondrocytes are enzymatically isolated from immature rabbits, and inoculated into the prosthetic articular cartilage devices essentially according to the protocol of Hemmen *(Orthopaedic. Trans.* (1991) 15:32) using $10^5$ cells/10 $\mu$l, 30 aliquots per 3.5 mm device. The cells are fed every second day with Hams F12 medium supplemented with 10% fetal calf serum (FCS) and antibiotic for three weeks. Chondrocyte growth throughout the template matrix is evaluated.

The present invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A prosthetic articular cartilage device comprising a dry porous volume matrix of biocompatible and at least partially bioresorbable fibers,
   said fibers selected from the group consisting of natural polymers, and analogs and mixtures thereof, said matrix being adapted to have an in vivo outer surface contour substantially the same as that of natural articular cartilage, said matrix having a pore size in the approximate range of about 100 microns to about 400 microns,
   whereby said matrix establishes a bioresorbable scaffold adapted for the ingrowth of articular chondrocytes, and for supporting natural articulating joint forces.

2. The prosthetic articular cartilage device of claim 1 further comprising crosslinks between at least a portion of said fibers.

3. The prosthetic articular cartilage device of claim 1 further comprising a plurality of polysaccharide molecules interspersed with said fibers.

4. The prosthetic articular cartilage device of claim 3 wherein at least a portion of said molecules provide crosslinks between ones of said fibers.

5. The prosthetic articular cartilage device of claim 1 wherein said fibers are selected from the group consisting of collagen, elastin, reticulin, cellulose, and mixtures thereof.

6. The prosthetic articular cartilage device of claim 3 wherein said fibers are present at a concentration of about 75 to 100% by dry weight, and said polysaccharide molecules are present at a concentration of about 0 to 25% by dry weight.

7. The prosthetic articular cartilage device of claim 3, wherein said polysaccharide molecules are selected from the group consisting of chondroitin 4-sulfate, chondroitin 6-sulfate, keratan sulfate, dermatan sulfate, heparan sulfate, heparin, hyaluronic acid, alginic acid, chitosan, and mixtures thereof.

8. The prosthetic articular cartilage device of claim 1, wherein said cartilage before implantation is a cylinder.

9. The prosthetic articular cartilage device of claim 2 wherein said crosslinks are formed by a chemical crosslinking agent.

10. The prosthetic articular cartilage device of claim 9 wherein said crosslinking agent is selected from the group consisting of glutaraldehyde, formaldehyde, biocompatible bifunctional aldehydes, carbodiimides, hexamethylene diisocyanate, bis-imidates, polyglycerol polyglycidyl ether, glyoxal, and mixtures thereof.

11. The prosthetic articular cartilage device of claim 3 wherein said cartilage has a density of about 0.07 to 0.50 gram matrix per cubic centimeter.

12. The prosthetic articular cartilage device of claim 3 wherein said cartilage has an intrafibrillary and interfibrillary space of about 2 to 14 cubic centimeters per gram matrix.

13. The prosthetic articular cartilage device of claim 1 wherein said fibers are oriented in a substantially random fashion throughout said matrix.

14. The prosthetic articular cartilage device of claim 1 wherein said fibers are oriented in a substantially ordered fashion throughout said matrix.

15. The Prosthetic articular cartilage device of claim 14 wherein said matrix comprises substantially circumferentially extending fibers.

16. The prosthetic articular cartilage device of claim 14 wherein said matrix comprises substantially radially extending fibers.

17. The prosthetic articular cartilage device of claim 1 wherein the density of said fibers is substantially uniform throughout said matrix.

18. The prosthetic articular cartilage device of claim 3 wherein said polysaccharide molecules are dispersed substantially uniformly throughout said matrix.

19. The prosthetic articular cartilage device of claim 3 wherein said polysaccharide molecules are dispersed nonuniformly throughout said matrix.

20. The prosthetic articular cartilage device of claim 1 further comprising a biocompatible conical base component including means for anchoring said articular cartilage device in a complimentary aperture in cancellous bone, said base component extending from portions of the outer surface of said matrix.

21. The prosthetic articular cartilage device of claim 20 wherein said base component is at least partially resorbable.

22. The prosthetic articular cartilage device of claim 20 wherein said base component includes a plurality of circumferentially extending ridges.

23. A method of regenerating articular cartilage in vivo comprising the steps of:
(a) providing prosthetic articular cartilage device comprising a dry porous volume matrix of biocompatible and bioresorbable fibers, said fibers selected from the group consisting of natural polymers, and analogs and mixtures thereof, said matrix being adapted to have an in vivo outer surface contour substantially the same as that of natural articular cartilage, and said matrix having a pore size in the approximate range of about 100 microns to about 400 microns; and
(b) implanting said prosthetic articular cartilage into a joint by surgical procedures, said matrix establishing a bioresorbable scaffold adapted for ingrowth of articular chondrocytes and for supporting natural articulating joint forces.

24. The method of claim 23 wherein said providing step includes providing a prosthetic articular cartilage device comprising crosslinked fibers.

25. The method of claim 23 wherein said providing step further comprises providing a prosthetic articular cartilage device including a plurality of polysaccharide molecules.

26. The method of claim 23 wherein said providing step further comprises providing a dry porous volume matrix further including a biocompatible conical base component for anchoring said matrix in a complementary aperture in cancellous bone, said base component extending from portions of the outer surface of said matrix.

27. The method of claim 26 wherein said providing step further comprises providing a dry porous volume matrix including a base component that is at least partially bioresorbable.

* * * * *